US006415016B1

United States Patent
Chornenky et al.

(10) Patent No.: US 6,415,016 B1
(45) Date of Patent: Jul. 2, 2002

(54) CRYSTAL QUARTZ INSULATING SHELL FOR X-RAY CATHETER

(75) Inventors: Victor I. Chornenky, Santa Rosa, CA (US); Ali Jaafar, Eden Prairie, MN (US); Graham S. Kerslick, Ithaca, NY (US)

(73) Assignee: Medtronic AVE, Inc., Santa Rosa, CA (US)

(*) Notice: Subject to any disclaimer, the term of this patent is extended or adjusted under 35 U.S.C. 154(b) by 0 days.

(21) Appl. No.: 09/756,287

(22) Filed: Jan. 9, 2001

(51) Int. Cl.$^7$ ................................................ H01J 35/00
(52) U.S. Cl. ........................ 378/122; 378/121; 378/65
(58) Field of Search ................................ 378/119, 121, 378/122, 65

(56) References Cited

U.S. PATENT DOCUMENTS

| | | | | |
|---|---|---|---|---|
| 3,688,150 A | * | 8/1972 | Wintzer | 313/558 |
| 5,012,102 A | * | 4/1991 | Gowlett | 250/352 |
| 5,383,467 A | | 1/1995 | Auer et al. | 128/664 |
| 5,582,171 A | | 12/1996 | Chornenky et al. | 128/653.1 |
| 5,713,853 A | | 2/1998 | Clark et al. | 604/53 |
| 5,776,100 A | | 7/1998 | Forman | 604/102 |
| 5,854,822 A | | 12/1998 | Chornenky et al. | 378/122 |
| 5,904,670 A | | 5/1999 | Schreiner | 604/280 |
| 5,925,016 A | | 7/1999 | Chornenky et al. | 604/96 |
| 6,069,938 A | | 5/2000 | Chornenky et al. | 378/122 |
| 6,095,966 A | | 8/2000 | Chornenky et al. | 600/3 |
| 6,108,402 A | | 8/2000 | Chornenky | 378/119 |
| 6,148,061 A | | 11/2000 | Shefer et al. | 378/121 |
| 6,275,566 B1 | * | 8/2001 | Smith et al. | 378/122 |

OTHER PUBLICATIONS

"Synthetic quartz crystal–Specifications and guide to the use," International Standard, Second Edition, CEI, 1993–04, Entire Document, see especially p. 52.

Sorrell, Charles et al., "Thermal Expansion and the High–Low Transformation in Quartz. II. Dilatometric Studies*," J. Appl. Cryst., vol. 7, No. 2, 1974, pp. 468–473.

von Hippel, A. et al., "Electric Breakdown of Glasses and Crystals as a Function of Temperature*," Physical Review, vol. 59, May 15, 1941, pp. 820–823.

U.S. application No. 08/701,764, Chornenky et al., filed Aug. 1996.

U.S. application No. 08/806,244, Chornenky et al., filed Feb. 1997.

U.S. application No. 09/760,815, Chornenky et al., filed Jan. 2001.

Ward, Roger W., "The Constants of Alpha Quartz," 14$^{th}$ Piezoelectric Devices Conference and Exhibition, Sep. 15–17, 1992, Sponsored by Components Group EIA, 1992, (See especially Table I, pp. 3–4).

* cited by examiner

Primary Examiner—Robert H. Kim
Assistant Examiner—Glen Kao
(74) Attorney, Agent, or Firm—Sterne Kessler Goldstein & Fox P.L.L.C.

(57) ABSTRACT

An insulating housing shell for a miniature x-ray emitter is provided. The housing shell is cut from a quartz monocrystal which is a suitable material for the insulating housing shell due to its resistivity and dielectric strength properties. The x-ray emitter can be inserted into a subject's body to deliver x-ray radiation. The emitter includes a cable, having a proximal and a distal portion. The insulating housing shell is coupled to the distal portion of the cable, and an anode and a cathode are disposed within the insulating housing shell. The cathode has a granular surface and is operative with the anode and the connector to produce the x-ray radiation. The cathode is composed of a material that also allows it to act as a getter.

12 Claims, 1 Drawing Sheet

CRYSTAL QUARTZ INSULATING SHELL FOR X-RAY CATHETER

CROSS-REFERENCE TO RELATED APPLICATIONS

Not applicable.

STATEMENT REGARDING FEDERALLY-SPONSORED RESEARCH AND DEVELOPMENT

Not applicable.

REFERENCE TO MICROFICHE APPENDIX/SEQUENCE LISTING/TABLE/COMPUTER PROGRAM LISTING APPENDIX (submitted on a compact disc and an incorporation-by-reference of the material on the compact disc)

Not applicable.

BACKGROUND OF THE INVENTION

1. Field of the Invention

The present invention is directed to an x-ray device having a cold cathode. More particularly, the present invention relates to a housing for a miniature x-ray device having a cold cathode and method for fabrication.

2. Background Art

Doctors and scientists continually strive to find less invasive ways to treat patients. Using treatments that are less intrusive to a patient's body, doctors can greatly reduce stress on the patient's system. For example, laparoscopic techniques enable physicians to explore the interior of the body and perform surgery through a small opening in the skin. Less intrusive medical techniques are extremely beneficial when applied to cardiovascular diseases, reflux disease of the esophagus, and other diseases of vessels, cavities and lumens of the body. To that end, catheters and like devices have been developed to traverse the human cardiovascular or circulatory system. Such devices have the capability to enter small blood vessels with diameters of about two to four millimeters, and make hairpin turns along tortuous paths within the vasculature.

Many types of catheters have been developed to deliver medication, such as, Heparin, Dexamethasone, and the like, to treat cardiovascular diseases, such as, stenosis, restenosis and the like. Catheters have also been used to provide beta-irradiation along the wall of a blood vessel to treat illnesses such as, restenosis. Moreover, catheters have been applied to the esophagus to treat gastroesophageal reflux disease (GERD). Many other disorders could be treated with small, effective medical devices capable of accessing the interior of the body.

A typical x-ray catheter includes a coaxial cable and miniature x-ray emitter connected to the distal end. The x-ray emitter consists of an anode and cathode assembly mounted in a miniature vacuum tube. To activate the x-ray catheter, a high DC or pulse voltage (e.g., fifteen to thirty-five kilovolts (kV) range) is applied to the tube. At the cathode surface, a high electric field results in the electron field emission from the cathode. The electrons are emitted into a vacuum gap between the anode and the cathode, and are accelerated by the electric field. As the accelerated electrons strike the anode, X-ray radiation is produced from the electrons.

The proximal end of the coaxial cable is connected to a high voltage power source. Outside the patient's body, the cable is secured to a pullback device, which moves the emitter along the blood vessel or another body cavity as it is being irradiated.

To be maneuverable within body cavities and blood vessels, it is desirable to use as small an x-ray device as possible. Miniaturization of x-ray emitters, however, imposes very stringent requirements on the dielectric strength and resistivity of the material that is required for the insulating shell. For coronary use, the wall thickness of the emitter should be as thin as 150–200 microns, and still be able to hold about thirty kV in voltage. This, in turn, requires the dielectric strength of the shell material to range between 150 to 200 kV/mm.

Very few dielectric materials can satisfy these requirements. For instance, ceramics, conventionally, have been used for insulation because they are relatively inexpensive, but they are ineffective for high voltage applications. Boron nitride is another conventional insulating material. However, boron nitride has poor vacuum integrity. Boron nitride is also a soft, mechanically weak material that is prone to cracking at the brazing joints. By using a long and sophisticated chemical vapor deposition (CVD) process, diamonds can be grown in special chambers to meet the resistivity and dielectric strength requirements. Although CVD diamonds have low thermal expansion properties, CVD diamonds have low absorption of x-ray and are not very accessible or machinable due to the CVD process.

What is needed, therefore, is an insulating material for the housing of an x-ray emitter that reduces cracking, and is easy and inexpensive to produce.

BRIEF SUMMARY OF THE INVENTION

The present invention is directed to an insulating housing shell used to encase a miniature x-ray emitter. In a preferred embodiment, the housing shell is cut from a quartz monocrystal along its z-axis.

The x-ray emitter is suitable for inserting into a subject's body and delivering x-ray radiation. The emitter includes a coaxial cable, having a proximal and a distal portion. The distal portion of the cable is coupled to the crystalline quartz housing shell. The housing shell provides a vacuum chamber enclosing an anode and a cathode disposed therein. The cathode has a granular surface and is operative with the anode and the cable to produce the x-ray radiation. The cathode is composed of a material that also allows it to act as a getter. The cathode can also include a diamond film on its surface that facilitates cold electron emission.

An advantage of the present invention is that crystalline quartz housing is compatible with existing brazing, soldering or other bonding technologies. This permits the vacuum chamber to be easily fabricated by known or future developed brazing, soldering or other bonding techniques.

Another advantage of the present invention is that the resistivity and dielectric strength properties of crystalline quartz do not substantially degrade or crack at higher temperatures.

Another advantage of the present invention is that crystalline quartz is easily accessible and machinable.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the pertinent art to make and use the invention. In the drawings, like reference numbers indicate identical or functionally similar elements. Additionally, the leftmost digit(s) of a reference number identifies the drawing in which the reference number first appears.

DETAILED DESCRIPTION OF THE INVENTION

The present invention is directed to an insulating housing shell for a device, and method of fabrication thereof, that irradiates passages, lumens, vessels, cavities, or interior sites in a subject's body with x-ray radiation. The device of the present invention is particularly advantageous in treating restenosis and stenosis of the cardiovascular vessels, gastroesophageal and gastrointestinal systems, and other ailments where delivery of localized x-ray radiation to interior portions of the body has been discovered to be effective. In an embodiment, the x-ray device can be introduced into the subject through an introducer or trocar.

Many disease states of the body involve the abnormal thickening of a lumen or passage. The x-ray device of the present invention provides a very promising way to treat these types of conditions. The x-ray device produces ionizing radiation that penetrates controllable depths of the cells on the surface of the passage or lumen. This radiation induces apoptosis, or programmed cell death.

X-ray radiation has been found to reduce the occurrence of restenosis when x-ray radiation is applied to area of a blood vessel where an angioplasty or other expansion of the vessel has taken place. In coronary applications, it is desirable to have the x-ray radiation penetrate into the adventitia tissue of the blood vessels about 0.5 to 1.0 mm in depth. Penetration into the cardiac muscle tissue should be minimized.

In one aspect of the present invention, an x-ray device positioned in the esophagus is used to treat Barrett's esophagus by inducing apoptosis in the abnormal cells of the epithelium. The use of the x-ray device of the present invention can therefore be used to reduce the escalation of this condition to cancer. Further, the x-ray device of the present invention can be used for preventing the thickening of the pylorus after dilatation of pyloric strictures.

When treating the interior of the body, it is desirable to use as small a device as possible. Very small devices are required when traversing the blood vessels of the cardiovascular system, for example. A smaller device will be more easily guided to the site of treatment. It is also important to minimize the occlusion of the blood vessel, in order to allow blood flow to the greatest extent possible.

Figure 1:
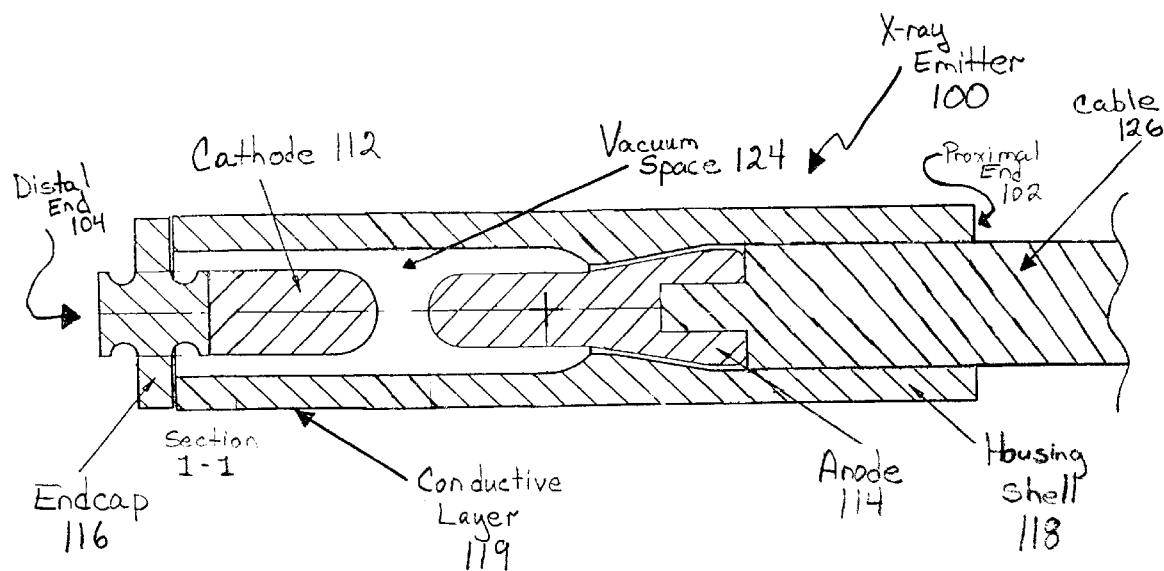
FIG. 1 illustrates a cross-sectional view, taken along a line 1—1 of FIG. 1A, of an x-ray emitter according to an embodiment of the present invention.
Figure 1A:
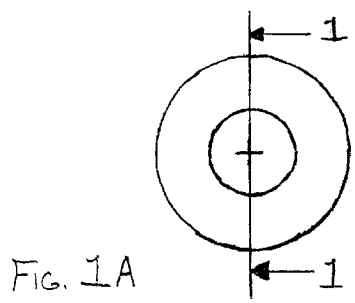
FIG. 1A illustrates a perspective view of the x-ray emitter of FIG. 1.

FIG. 1 and FIG. 1A illustrate an x-ray emitter 100 according to an embodiment of the present invention. X-ray emitter 100 has aproximal end 102 and a distal end 104, and includes a cathode 112, an anode 114, an endcap 116, and a housing shell 118. Anode 114, endcap 116, and housing shell 118 define a vacuum chamber which encloses a vacuum space 124. In order to produce x-ray radiation, an electrical field is applied across cathode 112 and anode 114, resulting in the emission of electrons from cathode 112 and acceleration of these electrons toward anode 114. Anode 114 consists of a heavy metal that causes the electrons to consistently produce x-ray radiation when the high-speed electrons are incident upon anode 114.

The x-ray radiation is emitted and travels through housing shell 118 which is moderately transparent to x-rays. The x-ray radiation is low energy below eight kiloelectron volts (keV), and must be filtered to avoid overly radiating the surface of the blood vessel. Housing shell 118 (described in detail below) performs this function. Anode 114 and cathode 112 are separated by a gap that varies depending on the requirements of the particular application. For many coronary applications, the gap can range from 0.20 to 1.5 mm. It would be apparent to one skilled in the relevant art(s) that gaps within a variety of ranges can be used depending on the particular application.

X-ray emitter 100 can be supplied with a high voltage by a cable 126, such as a coaxial cable and the like. Proximal end 102 of x-ray emitter 100 can be coupled to cable 126, such that the distal end of cable 126 is disposed within the body during treatment. A proximal end of cable 126 emerges from the body and can be coupled to a voltage generator (not shown).

It is desirable to maintain a vacuum condition within housing shell 118. In order to create the vacuum chamber, frequently, the components are assembled within a vacuum or the chamber is evacuated by conventional methods to create a vacuum. Further, a getter can also be disposed within housing shell 118. The getter can include zirconium, aluminum, vanadium, iron, and/or titanium. In an embodiment, the getter materials can be composed of an alloy including vanadium, iron and zirconium. One successful choice for the getter is a material produced by SAES and referred to as ST707. The SAES ST707 alloy getter is produced by thermal diffusion bonding and is composed of 24.6% vanadium, 5.4% iron, and 70% zirconium.

The getter has an activation temperature at which it will react with stray gas molecules in a vacuum. For example, the SAES ST707 alloy getter has an activation temperature of 400–500 degrees Celsius (C). Before the getter is activated, it is covered with a layer of oxidation that shields the getter material from the atmosphere at normal conditions. When the getter is heated to its activation temperature in a vacuum, the oxidation layer diffuses into the interior of the getter, revealing the active getter surface, which will react and bond with any stray gas molecule. The getter, therefore, eliminates stray gas molecules, thereby improving the quality of the vacuum within housing shell 118 up to $10^{-7}$ to $10^{-8}$ Torr.

It can be shown that a getter serves as an electron emitter when a voltage differential is applied. Therefore, in an embodiment, the getter is used as cathode 112. This combination of elements results in a smaller x-ray device with a very simple design. Accordingly, the getter must be sufficiently conductive and capable of electron emission to serve as an effective cathode at moderate electrical fields, for example, ten volts per micron to sixty volts per micron.

As described, a getter cathode 112 can be composed of many different types of getter materials. In an embodiment, cathode 112 consists of granular getter materials. The granulated surface of cathode 112 provides multiple microprotrusions capable of efficient field emission of electrons at moderate electrical fields. Using granular getter materials, field emission current densities of approximately 0.5 to 5 milliamps per square millimeter are observed at cathode 112 at electrical fields of ten to fifty volts per micron. This level of emission current is similar to that found in diamond-coated cathodes at electrical fields that are moderate for x-ray production. Therefore, when cathode 112 is made of granular metal materials, cathode 112 typically does not require an additional coating, such as a diamond film, in order to emit electrons at moderate electrical fields for x-ray applications. Moreover, a device using a granular getter material as cathode 112 is considerably less complicated to manufacture. Cathode 112 with microprotrusions can be formed by thermal diffusion bonding of granulated getter material, or getter powder, having granular sizes of 0.5 to 50 micrometers in diameter.

In an embodiment of the present invention, x-ray radiation is produced while keeping the required electrical fields low by mixing titanium carbide or, preferably, a diamond powder with the granulated getter materials before forming cathode 112. Diamond materials display valuable properties as field emitters, losing electrons easily as a field is applied. Where a diamond powder is included in cathode 112, an electrical field of ten to fifty volts per micron will produce current densities in the range of one to ten milliamps per millimeter square. The diamond material can be purchased commercially from numerous sources. Most of the powder diamond material is obtained from laser deposition that can be performed at room temperature, although it can be produced from natural beds of diamond.

In an embodiment of the present invention, the field emission properties of cathode 112 can be modified by a conditioning procedure that alters the surface of cathode 112 to achieve predetermined field emission parameters. Multiple applications of high voltage are carried out at different distances and relative positions of the electrodes, causing electrical discharges between electrodes. The discharges destroy unstable emitting sites at cathode 112 surface and drive the field emission parameters into the desired range. As a result, a conditioned cathode 112 is capable of more efficient and consistent performance. Conditioning of cathode 112 can be carried out according to the concepts set forth in High Voltage Vacuum Insulation: Basic Concepts and Technological Practice, R. V. Latham, Editor, Academic Press, 1995.

Spark conditioning and current conditioning can be used to improve cathode 112 in an embodiment of the present invention. The slow application of voltage involved in current conditioning can be the most preferable method for conditioning cathode 112. Current conditioning involves slow increases in the application of voltage across cathode 112 and anode 114. Voltage application can begin at about one kilovolt per millimeter and gradually increase to about sixty kilovolts per millimeter, and perhaps as high as 100 kilovolts per millimeter. The voltage application can increase in increments of one kilovolt per millimeter in an embodiment of the present invention. The procedure for conditioning cathode 112 can take about thirty minutes. The conditioning process can be carried out before cathode 112 is assembled with the housing.

The slow application of increasing voltage gradually melts the microprotrusions present on cathode 112. The sharpest field-emitting microprotrusions can be thermally blunted following excessive electron emission brought on by the current conditioning.

While attempting to produce x-ray radiation of about eight to ten keV in the body, it is important to keep the magnitude of the electrical fields at the surface of cathode 112 low enough to prevent arcing between anode 114 and cathode 112. Just on the other side of housing shell 118 from anode 114 and cathode 112, a conductive layer 119 is held at ground. An electrical discharge from the surface of cathode 112 to anode 114 along the inside surface of housing shell 118 is teimed an electric flashover. An electric flashover must be prevented to keep x-ray emitter 100 operative. According to the present invention, the probability of flashover is reduced by configuring cathode 112 and endcap 116 to be shielded at the point at which they meet. Moreover, diamond-coated field electron emissions start at a lower electrical field. Therefore, the emissions are more stable.

Due to concerns about bulk breakdown attributed to vacuum and material breakdown and flashover, dielectric strength is an important consideration for choosing a material for housing shell 118. The dielectric strength is the maximum electric field that a material can withstand before breaking down. However, surface discharge can occur at lower electrical field strengths. Many individual factors affect the flashover voltage, such as the surface geometry, material contamination, the material history, and vacuum quality.

The ability to lower the required electric field at cathode 112 results in a less expensive manufacturing technique. Small irregularities on the surface of cathode 112 result in an increase in the magnitude of the electrical field for an applied voltage, thereby increasing the chance of electrical flashover. The weaker the required electrical field at cathode 112, the more imperfections can be tolerated on cathode 112 surface without risking vacuum breakdown from unstable emission sites.

Heat is generated by the operation of x-ray emitter 100. Therefore, it is important that the coefficients of thermal expansion (CTEs) are similar in all materials used to construct x-ray emitter 100. If materials having inconsistent CTEs are used, the integrity of the vacuum chamber of x-ray emitter 100 can be jeopardized. In an embodiment of the present invention, endcap 116 is composed of molybdenum, having a coefficient of thermal expansion (CTE) of $4.9 \times 10^{-6}$ per degrees C. However as intimated above, endcap 116 can be composed of any material having a CTE that is consistent with the CTE of housing shell 118 to preserve the vacuum seal. The CTE of anode 114 is also important because it seals proximal end 102 of housing shell 118. Therefore, in an embodiment, anode 114 can be comprised of tungsten, having a CTE of $4.6 \times 10^{-6}$ per degrees C. Other materials and combinations of materials having similar properties and comparable coefficients of thermal expansion could be used.

Another consequence of heat generation is that cooling can be desirable in some situations. Where x-ray emitter 100 is used in a blood vessel, the blood flow past x-ray emitter 100 is sufficient to dissipate the generated heat. Where the x-ray emitter 100 is used in the esophagus or other cavity, a fluid could circulate through a balloon surrounding x-ray emitter 100 to prevent damage to the body.

In an embodiment, the elements of x-ray emitter 100 are bonded together using vacuum brazing. A brazing alloy joins cathode 112 to endcap 116. Further a brazing alloy connects endcap 116 to housing shell 118. Additional brazing alloy bonds anode 114 to housing shell 118. The vacuum brazing techniques are important to maintaining the integrity of the vacuum chamber. Vacuum brazing as used in x-ray emitter 100 can be provided by Koral Labs, Minneapolis, Minn., for example. Two examples of preferred brazing alloys are AuSn and AuGe. While this embodiment describes a preferred method for bonding the elements, it should be understood that any presently available or future developed bonding technique or methodology, including, but not limited to, soldering, welding, epoxy, other adhesives and the like, can be used to attach the elements or seal housing shell 118.

The shape of cathode 112 affects the electron emission qualities of cathode 112. Cathode 112 can be cylindrically shaped with a half full sphere shape on one end. Alternatively, cathode 112 can have a standard 118 degree drill point at the tip of one end.

In order to apply an electric field across anode 114 and cathode 112, a coaxial cable can be used as cable 126. The coaxial cable 126 can be coupled to a high-voltage generator at a proximal end of cable 126 that remains outside the body. The distal end of coaxial cable 126 can be coupled to x-ray emitter 100. An internal conductor of coaxial cable 126 can be coupled to anode 114 at the appropriate voltage. An external conductive layer of coaxial cable 126 can be held at ground and coupled to cathode 112 base via a conductive solder. Other methods can also be used to apply the electric field across anode 114 and cathode 112 as would be apparent to one skilled in the relevant art(s).

Coaxial cable 126 used in conjunction with the present invention must be able to carry the required voltages, have sufficient flexibility to make sharp turns as it follows the path of an interior passage of the body, and have a sufficiently small diameter to traverse the area of the body to be treated. Standard high voltage coaxial cables are generally not flexible enough. However, miniature high frequency coaxial cables with an outer diameter of approximately one millimeter to three millimeters generally exhibit sufficient flexibility. These -types of cables are typically used in high frequency applications at voltages less than several kilovolts. Such cables have been discovered to hold direct current voltages as high as 75–100 kV without breakdown. Therefore, these cables are well suited for use with x-ray emitter 100. In an embodiment, a cable with an outer diameter less than or equal to three millimeters is used as cable 126. In another embodiment, cable 126 has an outer diameter of one to two millimeters. Such cables are manufactured by, for example, New England Electric Wire Corporation, Lisborn, N.H.

Housing shell 118 of x-ray emitter 100 is substantially transparent to x-rays in order to allow a full dosage to reach a treatment site. Housing shell 118 is an electrical insulator, capable of supporting x-ray emitter 100 without electrical discharge between the exterior of housing shell 118 at ground and the interior of housing shell 118 at high voltage. A biocompatible coating of a polymeric material, such as, polyethylene, polyurethane or Teflon®, for example is applied to the external surfaces of housing shell 118. Housing shell 118 can be composed of CVD boron nitride, CVD silicon nitride, beryllium oxide, aluminum oxide, or other such metals or ceramic material. Housing shell 118 can also be composed of a CVD diamond three-dimensional structure. However, as discussed, these materials have several drawbacks, namely they lack the requisite dielectric strength or are too expensive to manufacture, for high voltage applications.

In a preferred embodiment, crystalline quartz is used to fabricate housing shell 118. Crystalline quartz refers to natural or man-made $SiO_2$ in crystalline form (also known as monocrystal quartz). Crystalline quartz has a dielectric strength of about 600 kV/mm that does not drop as temperature increases. As described above for coronary applications, the thickness of housing shell 118 should be as thin as 150–200 microns, and capable of holding about thirty kV in voltage with a dielectric strength ranging between 150 to 200 kV/mm. It can be shown that the dielectric strength of 200 microns thick crystalline quartz plates is higher than 175 kV/mm, which meets the dielectric strength requirements.

The resistivity for crystalline quartz is $10^{16}$ ohms-cm. In comparison to CVD diamonds, crystalline quartz has a higher absorption of x-ray, but is more inexpensive, accessible and machinable than a diamond-based insulating shell.

Figure 2:
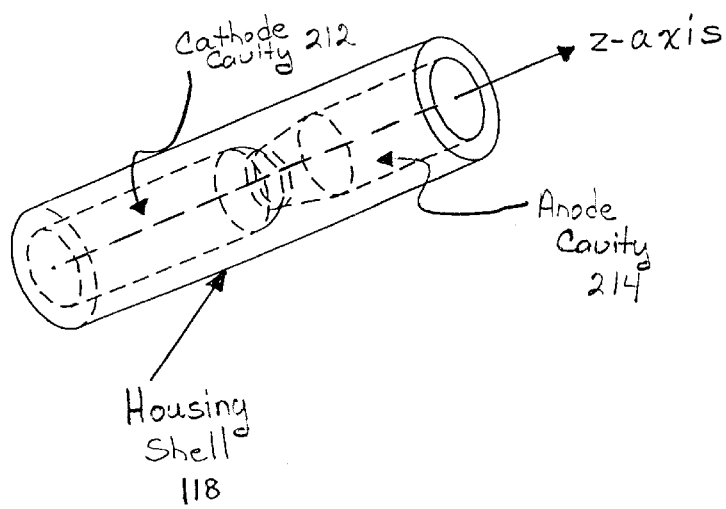
FIG. 2 illustrates an insulating housing shell according to an embodiment of the present invention.

A method for producing a device suitable for insertion into a body and delivering x-ray radiation is also contemplated by the present invention. First, housing shell 118 is machined or cut from crystalline quartz using conventional techniques. FIG. 2 illustrates housing shell 118 cut from crystalline quartz according to an embodiment of the present invention. As shown, housing shell 118 is cut from the crystalline quartz with the z-axis parallel to the axis of housing shell 118. A z-cut is apreferred cut to ensure housing shell 118 satisfies the dielectric strength and resistivity requirements. At a temperature ranging from room temperature to 550 degrees C, crystalline quartz has a CTE of $12 \times 10^{-6}$ per degrees C along the direction parallel to z-axis. In the direction perpendicular to the z-axis, the CTE is $20 \times 10^{-6}$ per degrees C.

After housing shell 118 has been cut to the desired length, cathode cavity 212 and anode cavity 214 are formed, using conventional techniques. Next, a structure for cathode 112, including molded granular getter material, and anode 114 are provided. This method of manufacture provides the advantage of simplicity because cathode 112 and getter components are present in the same structure. Cathode 112 and anode 114 are then enclosed in a vacuum housing so that cathode 112 is operative with anode 114 to produce x-ray radiation. All vacuum sealing procedures are recommended to be performed at temperatures below 500 degrees C to 550 degrees C. Typically, crystalline quartz incurs a phase transition at 575 degrees C with a significant volume change, which can cause cracking of the crystal under thermal stresses.

In an embodiment, to seal quartz-based x-ray emitter 100, the brazing surfaces of housing shell 118 at the conical surface of anode 114 and the surface endcap 116 are preliminary metallized by using techniques known to those skilled in the relevant art(s). Next, a 450 degrees C to 550 degrees C brazing process is applied for the final sealing of x-ray emitter 100. Thus, crystalline quartz is compatible with existing brazing and like bonding technologies.

As described above, the CTEs of the other components of x-ray emitter 100 should be consistent with the CTE of quartz-based housing shell 118 to maintain the integrity of the vacuum chamber of x-ray emitter 100. Therefore, the CTE for the material used to compose endcap 116 can range from $5 \times 10^{-6}$ per degrees C to $13 \times 10^{-6}$ per degrees C. In an embodiment, gold having a CTE of $14.2 \times 10^{-6}$ per degrees C is used as the material for anode 114. In another embodiment, copper having a CTE of $16.6 \times 10^{-6}$ per degrees C is used as the material for anode 114. In another embodiment, nickel having a CTE of $13 \times 10^{-6}$ per degrees C is used as the material for anode 114. The nickel can be coated with gold to produce a heavier metal and increase the efficiency of the radiation.

While various embodiments of the present invention have been described above, it should be understood that they have been presented by way of example, and not limitation. It will be apparent to persons skilled in the relevant art(s) that various changes in form and detail can be made therein without departing from the spirit and scope of the invention. Thus, the present invention should not be limited by any of the above described exemplary embodiments, but should be defined only in accordance with the following claims and their equivalents.

What is claimed is:

1. A device for use in delivering x-ray radiation, comprising:
   a crystalline quartz housing shell;
   an anode disposed within said crystalline quartz housing shell; and
   a cathode disposed within said crystalline quartz housing shell, wherein said cathode is operative with said anode to produce the x-ray radiation.

2. The device of claim 1, wherein said crystalline quartz housing shell is cut from a quartz monocrystal having a z-axis parallel to the axis of said crystalline quartz housing shell.

3. The device of claim 1, wherein said cathode comprises at least one of a granular surface and a material that allows said cathode to act as a getter.

4. The device of claim 1, wherein said anode comprises a heavy metal.

5. The device of claim 1, wherein said anode is composed of at least one of gold and nickel.

6. The device of claim 1, wherein said anode is composed of copper.

7. The device of claim 1, further comprising:
   a cable coupled to a proximal end of said crystalline quartz housing shell.

8. An x-ray catheter capable of being introduced into a subject through an introducer or trocar, comprising:
   a housing shell;
   an anode disposed within said housing shell; and
   a cathode disposed within said housing shell, wherein said housing shell is a crystalline quartz.

9. A method for producing a device suitable for use in delivering x-ray radiation, comprising the steps of:
   fabricating a structure composed of crystalline quartz;
   forming a hollow chamber within the structure;
   disposing a cathode within the hollow chamber, the cathode including granular getter material;
   disposing an anode within the hollow chamber, such that the anode and the cathode are separated by a gap, and attaching an endcap, the endcap and the anode being disposed at opposing ends of the structure to produce a vacuum chamber from the hollow chamber, the vacuum chamber encasing the cathode, whereby the cathode is operative with the anode to produce the x-ray radiation.

10. The method of claim 9, wherein said fabricating step comprises cutting crystalline quartz along a z-axis to fabricate the structure, whereby the z-axis is parallel to the axis of the structure.

11. The method of claim 9, further comprising the step of:
    mixing a diamond powder with the granulated getter material prior to forming the cathode for placement in the structure.

12. The method of claim 9, wherein said attaching step is performed at temperatures below 500 degrees C to 550 degrees C to produce the vacuum chamber.

* * * * *